US009028396B2

(12) United States Patent
Minetoma

(10) Patent No.: US 9,028,396 B2
(45) Date of Patent: May 12, 2015

(54) ENDOSCOPE SYSTEM, PROCESSING UNIT THEREFOR, AND IMAGE PROCESSING METHOD

(75) Inventor: Yasuhiro Minetoma, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 223 days.

(21) Appl. No.: 13/335,733

(22) Filed: Dec. 22, 2011

(65) Prior Publication Data

US 2012/0197076 A1    Aug. 2, 2012

(30) Foreign Application Priority Data

Jan. 27, 2011 (JP) .................................. 2011-015500

(51) Int. Cl.
| A61B 1/04 | (2006.01) |
| A61B 1/06 | (2006.01) |
| A61B 1/00 | (2006.01) |
| A61B 1/05 | (2006.01) |
| A61B 1/313 | (2006.01) |
| A61B 5/00 | (2006.01) |

(52) U.S. Cl.
CPC ........... *A61B 1/0638* (2013.01); *A61B 1/00009* (2013.01); *A61B 1/05* (2013.01); *A61B 1/0646* (2013.01); *A61B 1/3137* (2013.01); *A61B 5/489* (2013.01); *A61B 1/063* (2013.01); *A61B 1/0653* (2013.01)

(58) Field of Classification Search
CPC ................................................ A61B 1/00009
See application file for complete search history.

(56) References Cited

U.S. PATENT DOCUMENTS

| 7,247,135 B2 * | 7/2007 | Iriyama .......................... 600/181 |
| 7,539,335 B2 * | 5/2009 | Fukuyama .................... 382/128 |
| 7,678,045 B2 * | 3/2010 | Igarashi ......................... 600/160 |

(Continued)

FOREIGN PATENT DOCUMENTS

| JP | 1-297042 A | 11/1989 |
| JP | 2000-148987 A | 5/2000 |

(Continued)

OTHER PUBLICATIONS

Notification of Reason(s) for Refusal dated Jan. 25, 2013, with English translation.

(Continued)

*Primary Examiner* — Alireza Nia
*Assistant Examiner* — Jae Woo
(74) *Attorney, Agent, or Firm* — McGinn IP Law Group, PLLC

(57) ABSTRACT

Broadband light and narrowband light are simultaneously projected toward a subject. The subject is imaged by a color CCD to obtain a blue signal, a green signal, and a green signal. A base image is generated from the signals of three colors. Based on a luminance ratio B/G between the blue signal and the red signal, a B/G image is generated. A high frequency component is extracted from the B/G image to obtain a superficial-blood-vessel extracted image, and a medium frequency component is extracted from the B/G image to obtain a middle-deep-blood-vessel extracted image. Based on the base image and one of the superficial-blood-vessel extracted image and the middle-deep-blood-vessel extracted image, a blood vessel emphasized/de-emphasized image, in which the superficial blood vessels or the middle-deep blood vessels are emphasized or de-emphasized, is generated. The blood vessel emphasized/de-emphasized image is displayed on a monitor.

12 Claims, 10 Drawing Sheets

(56) References Cited

U.S. PATENT DOCUMENTS

| | | | |
|---|---|---|---|
| 8,000,776 B2* | 8/2011 | Gono | 600/476 |
| 8,090,177 B2* | 1/2012 | Venkataraman et al. | 382/130 |
| 2003/0139650 A1* | 7/2003 | Homma | 600/181 |
| 2007/0027362 A1* | 2/2007 | Handa et al. | 600/160 |
| 2007/0263929 A1* | 11/2007 | Kaji | 382/168 |
| 2009/0036741 A1* | 2/2009 | Igarashi et al. | 600/160 |
| 2009/0040298 A1* | 2/2009 | Yamazaki et al. | 348/68 |
| 2009/0058999 A1* | 3/2009 | Gono et al. | 348/71 |
| 2009/0147999 A1* | 6/2009 | Maeda et al. | 382/106 |
| 2009/0247881 A1* | 10/2009 | Maeda et al. | 600/476 |
| 2009/0306478 A1* | 12/2009 | Mizuyoshi | 600/178 |
| 2011/0237915 A1* | 9/2011 | Yamaguchi | 600/339 |
| 2011/0270035 A1* | 11/2011 | Gono | 600/118 |

FOREIGN PATENT DOCUMENTS

| | | |
|---|---|---|
| JP | 3559755 B2 | 9/2004 |
| JP | 2009-254794 A | 11/2009 |

OTHER PUBLICATIONS

European Search Report date May 23, 2012.

* cited by examiner

ENDOSCOPE SYSTEM, PROCESSING UNIT THEREFOR, AND IMAGE PROCESSING METHOD

FIELD OF THE INVENTION

The present invention relates to an endoscope system for diagnosis focusing on superficial blood vessels, middle-deep blood vessels, and pit patterns in a subject, a processing unit therefor, and an image processing method.

BACKGROUND OF THE INVENTION

In a recent medical field, endoscopes are widely used for diagnoses and treatment. In order to inspect an inside of a subject with use of the endoscope, white or broadband light is used for illumination in a normal light observation mode. Besides, narrowband light having a limited wavelength range comes to be more frequently used for the sake of emphasizing blood vessels in the subject in a special light observation mode, as disclosed in Japanese Patent No. 3559755.

As the wavelength of the light to be projected toward the inside of the subject becomes longer, a depth of reach of the light in the subject tissues increases. According to Japanese Patent No. 3559755, with use of the above characteristics, blood vessels at a particular depth are emphasized. For example, upon projection of blue (B) narrowband light having a shorter wavelength and a shorter depth of reach, the superficial blood vessels can be emphasized. Upon projection of green (G) narrowband light having a longer wavelength and a longer depth of reach than the B light, the middle-deep blood vessels can be emphasized more than the superficial blood vessels.

For endoscopic diagnosis, in accordance with a diagnostic situation, diagnosis is performed with focusing on middle-deep blood vessels in some cases, and diagnosis is performed with focusing on superficial blood vessels in other cases. Besides, diagnosis is performed with focusing on information on protrusions and recesses such as pit patterns in living tissues, in addition to the information on the blood vessels, in some other cases. Consequently, it has been demanded that only the middle-deep blood vessels or only the superficial blood vessels are emphasized without deleting the information on protrusions and recesses in the living tissues, on a case-by-case basis, namely, in accordance with the diagnostic purpose. Furthermore, in the case where both of the superficial blood vessels and the middle-deep blood vessels are conspicuous, it is demanded that, only the blood vessels to be focused on are emphasized, and the blood vessels not to be focused on are de-emphasized.

With regard to the above demand, according to the description of Japanese Patent No. 3559755, although it is possible to emphasize the blood vessels at a particular depth, there is no disclosure about de-emphasizing of the other blood vessels. Additionally, according to the description of Japanese Patent No. 3559755, since the illumination light has a limited wavelength range, visibility of the blood vessel itself is increased, but visibility of the information on protrusions and recesses in living tissues other than blood vessels may be decreased due to shortage of light amount.

SUMMARY OF THE INVENTION

In view of the above, an object of the present invention is to provide an endoscope system capable of emphasizing or de-emphasizing superficial blood vessels or middle-deep blood vessels without deleting information on protrusions and recesses in living tissues, a processing unit for the electronic endoscope, and an image processing method.

In order to achieve the above and other objects, an endoscope system of the present invention includes an illumination device, an image capturing device, an image processing device, and a displaying device. The illumination device projects illumination light toward a subject. The image capturing device captures an image of light reflected from the subject. The image processing device generates a blood vessel emphasized/de-emphasized image, in which either first-layer blood vessels located at a predetermined depth or second-layer blood vessels located at a depth deeper than the first-layer blood vessels, or both of them are emphasized or de-emphasized, based on an imaging signal obtained by the image capturing. The displaying device displays the blood vessel emphasized/de-emphasized image.

The image processing device includes a base image generator, an extractor, and a blood vessel emphasized/de-emphasized image generator. The base image generator generates a base image for use in emphasizing/de-emphasizing of the first-layer blood vessels or the second-layer blood vessels based on the imaging signal. The extractor extracts either the first-layer blood vessels or the second-layer blood vessels from the imaging signal. The blood vessel emphasized/de-emphasized image generator generates a blood vessel emphasized/de-emphasized image, in which either the first-layer blood vessels or the second-layer blood vessels are selectively emphasized or de-emphasized, based on the base image and a blood-vessel extracted image containing either the first-layer blood vessels or the second-layer blood vessels extracted by the extractor.

The image capturing device captures an image of the subject by a color imaging element. The extractor includes a B/G image generating section and a blood vessel extracting section. The B/G image generating section generates a B/G image based on a luminance ratio between a blue signal outputted from a blue pixel of the imaging element and a green signal outputted from a green pixel of the imaging element. The blood vessel extracting section extracts either the first-layer blood vessels or the second-layer blood vessels from the B/G image. The blood vessel extracting section extracts a first frequency component containing the first-layer blood vessels from the B/G image so as to generate a first-layer-blood-vessel extracted image, or extracts a second frequency component containing the second-layer blood vessels from the B/G image so as to generate a second-layer-blood-vessel extracted image.

The illumination device projects broadband light and narrowband light toward the subject at the same time. The base image generator generates the base image based on the imaging signal obtained by capturing an image of the subject projected with the broadband light and the narrowband light at the same time. The base image generator generates the base image without using information on the narrowband light when a bandwidth of the narrowband light is wide. Further, the base image generator derives a first frequency component corresponding to the first-layer blood vessels by subjecting the imaging signal to frequency conversion, and when the first frequency component thus derived is lower than a predetermined value, the base image generator determines that resolution of the first-layer blood vessels is low, and generates the base image without using information on the narrowband light. The image capturing device captures an image of the subject by a color imaging element. The base image generator derives a correlation between an output value of a blue pixel of the imaging element and an output value of a green pixel of the imaging element in the imaging signal obtained by the image capturing, and when similarity between the output value of the blue signal and the output value of the green signal is high, the base image generator determines that resolution of the first-layer blood vessels is low, and generates the base image without using information on the narrowband light. When the resolution of the first-layer blood vessels is low, the base image generator generates the base image without using the output value of the blue pixel. Further, when the resolution of the first-layer blood vessels is low, the base image generator generates the base image based on the imaging signal obtained by projecting only the broadband light while stopping projection of the narrowband light at the time of image capturing.

The illumination device projects broadband light and narrowband light separately toward the subject in a sequential manner. The base image generator generates the base image based on a broadband signal obtained by capturing an image of the subject projected with the broadband light and a narrowband signal obtained by capturing an image of the subject projected with the narrowband light. Information on a blood vessel depth of the first-layer blood vessels and information on a blood vessel depth of the second-layer blood vessels are derived from a luminance ratio between the narrowband signal and the broadband signal.

The first-layer blood vessels are superficial blood vessels, and the second-layer blood vessels are middle-deep blood vessels.

With regard to a processing unit for an endoscope system of the present invention, the endoscope system includes an endoscope for capturing an image of a subject under illumination and the processing unit for processing an image. The processing unit includes a receiving device and an image processing device. The receiving device receives an imaging signal from the electric endoscope. The image processing device generates a blood vessel emphasized/de-emphasized image, in which either first-layer blood vessels located at a predetermined depth or second-layer blood vessels located at a depth deeper than the first-layer blood vessels, or both of them are emphasized or de-emphasized, based on the imaging signal.

An image processing method of the present invention includes an imaging-signal receiving step and an image generating step. In the imaging-signal receiving step, an imaging signal obtained by capturing an image of a subject projected with illumination light is received from an electric endoscope. In the image generating step, there is generated a blood vessel emphasized/de-emphasized image, in which either first-layer blood vessels located at a predetermined depth or second-layer blood vessels located at a depth deeper than the first-layer blood vessels, or both of them are emphasized or de-emphasized, based on the imaging signal.

According to the present invention, it is possible to emphasize or de-emphasize the superficial blood vessels or middle-deep blood vessels without deleting the information on protrusions and recesses in the living tissues.

DESCRIPTION OF THE DRAWINGS

The above objects and advantages of the present invention will become easily understood by one of ordinary skill in the art when the following detailed description of the preferred embodiments would be read in connection with the accompanying drawings, wherein.

DESCRIPTION OF THE PREFERRED EMBODIMENTS

Figure 1:
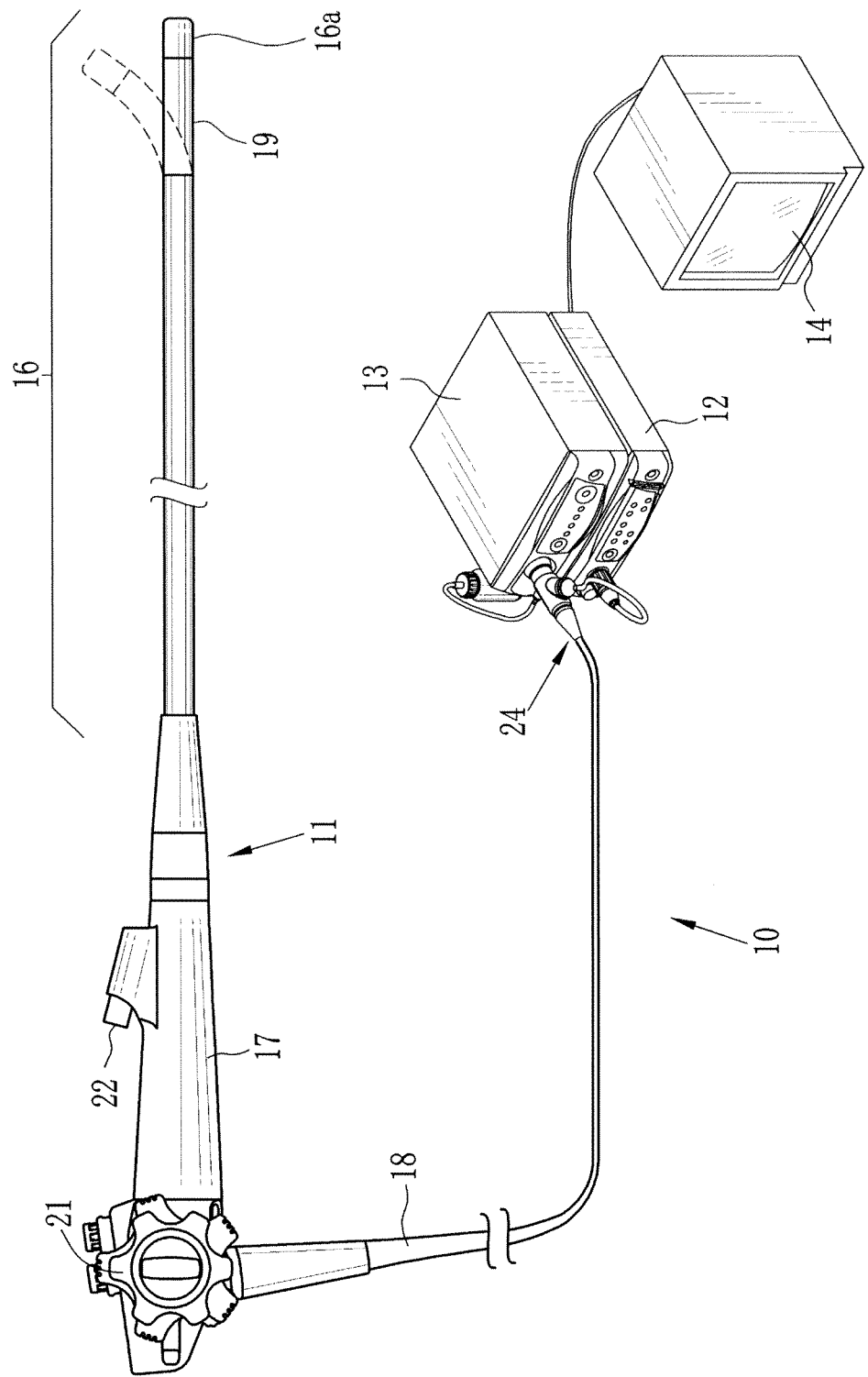
FIG. 1 is a diagram illustrating an outer appearance of an endoscope system.

As shown in FIG. 1, an electronic endoscope system 10 according to a first embodiment of the present invention includes an electronic endoscope 11, a processing unit 12, a light source unit 13, and a monitor 14. The electronic endoscope 11 captures an image of a body cavity of a subject. The processing unit 12 produces an endoscopic image based on a signal obtained by the image capturing. The light source unit 13 generates light for illuminating the body cavity. The monitor 14 displays the endoscopic image. The electronic endoscope 11 includes a flexible insertion section 16 to be inserted into the body cavity, an operating section 17 coupled to a proximal end of the insertion section 16, and an universal cord 18 for connecting the operating section 17 to the processing unit 12 and the light source unit 13.

A bending portion 19 constituted by a plurality of serially linked segments is formed at a distal end of the insertion section 16. The bending portion 19 curves in any directions in response to the operation on an angle knob 21 of the operating section 17. A distal portion 16a containing an optical system for capturing an image of the body cavity and the like is provided at a front portion of the bending portion 19. The distal portion 16a is oriented to any desirable direction in the body cavity in response to the curving operation of the bending portion 19.

The universal cord 18 has a connector 24 to be coupled to the processing unit 12 and the light source unit 13. The connector 24 is a complex connector consisting of a connector terminal for data communication and a connector terminal for light source. Through this connector 24, the electronic endoscope 11 is removably connected to the processing unit 12 and the light source unit 13. It is to be noted that the reference numeral 22 denotes a forceps opening for inserting tools for procedure.

Figure 2:
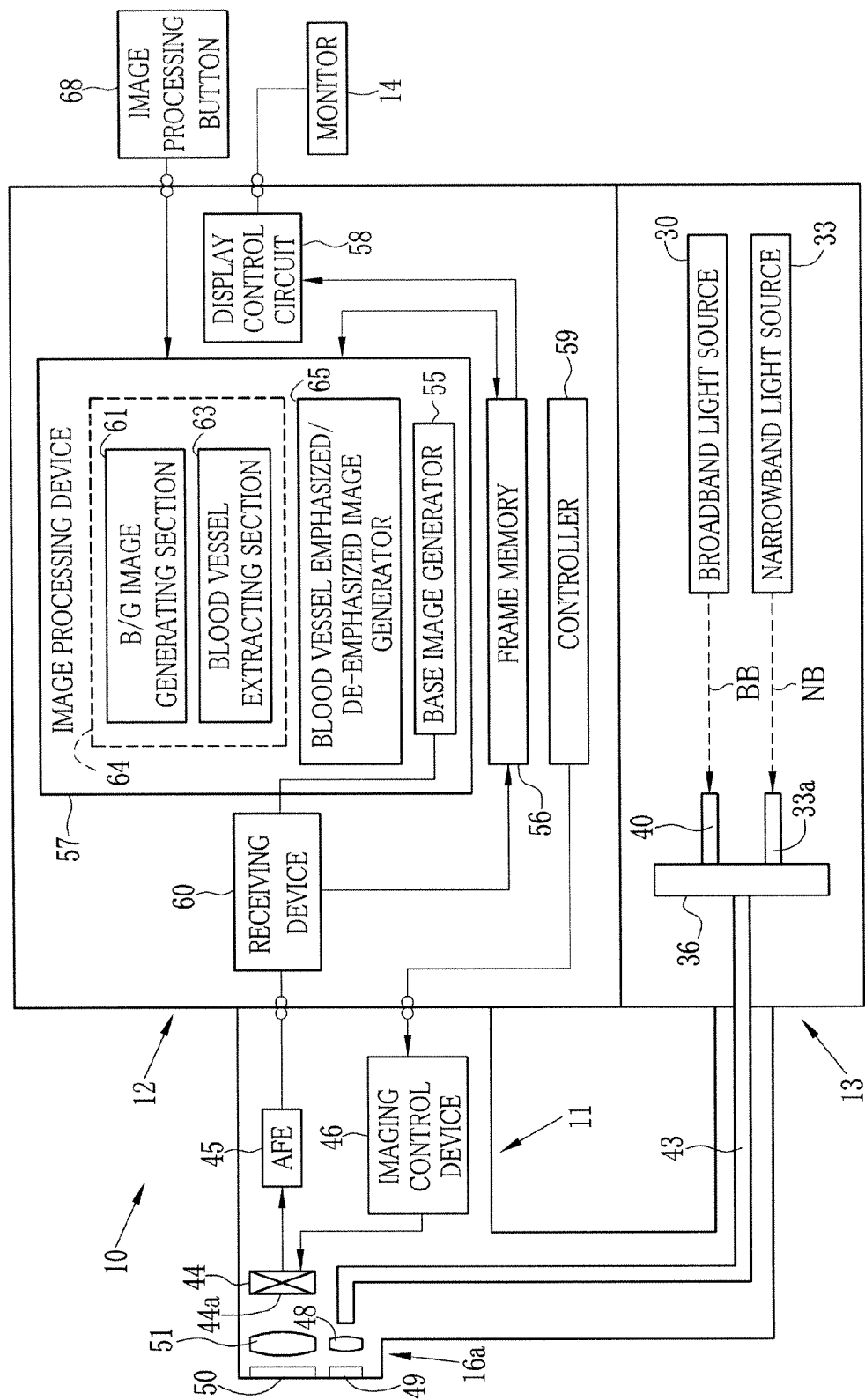
FIG. 2 is a block diagram illustrating an electrical configuration of the endoscope system according to a first embodiment of the present invention.
Figure 3:
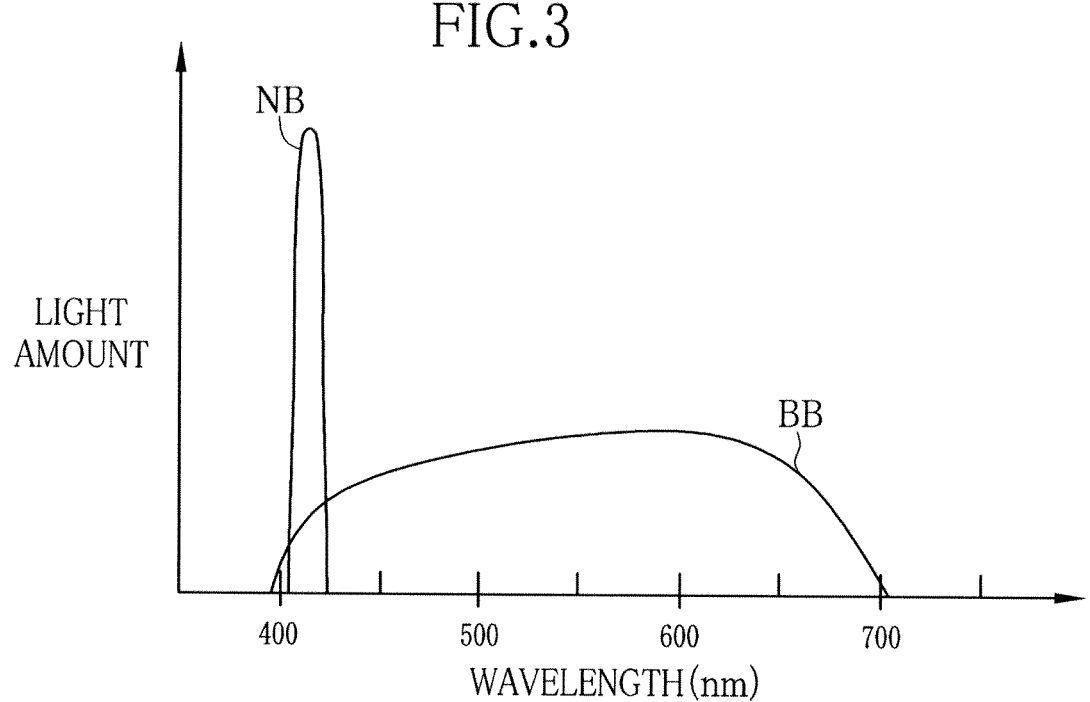
FIG. 3 is a graph showing emission spectra of broadband light and narrowband light.
Figure 4:
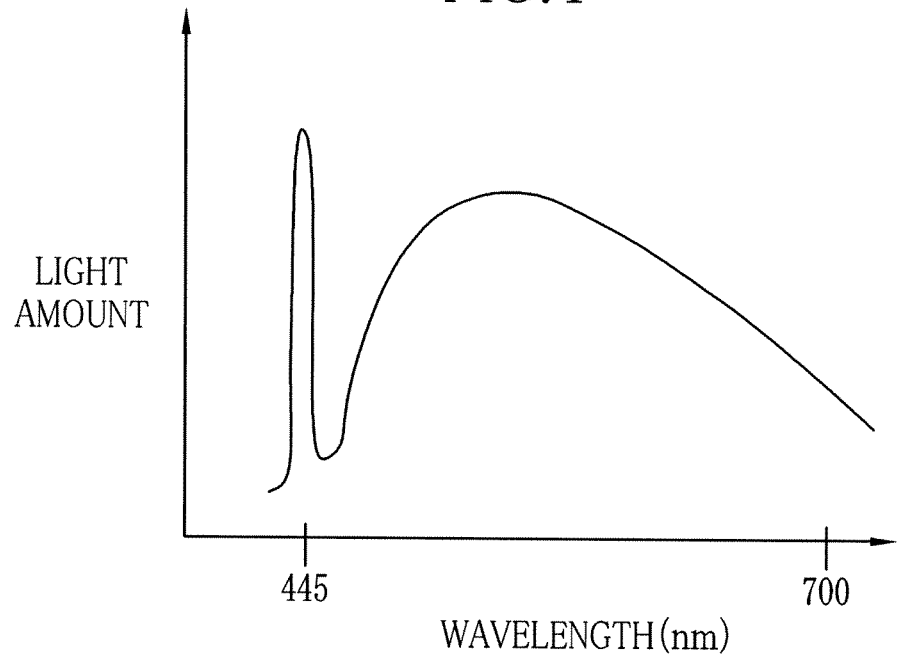
FIG. 4 is a graph showing emission spectrum of white light which is obtained by blue laser light and exciting light generated upon projecting the blue laser light onto a phosphor.

As shown in FIG. 2, the light source unit 13 includes a broadband light source 30, a narrowband light source 33, and a coupler 36. The broadband light source 30 emits broadband light BB having a wavelength ranging from a blue ray region to a red ray region (about 400 nm to 700 nm), as shown in FIG. 3. The broadband light source 30 is kept on while the electronic endoscope 11 is in operation. The broadband light BB emitted from the broadband light source 30 is introduced into a broadband optical fiber 40. It is to be noted that the broadband light BB may be white light emitted from a xenon lamp, or white light obtained by mixing laser light having a center wavelength of 450 nm and exciting light generated upon projecting the laser light onto a phosphor and having a wavelength of 460 nm to 700 nm. The emission spectrum of the white light is shown in FIG. 4.

The narrowband light source 33 may be light emitting diode (LED), laser diode (LD), or the like. As shown in FIG. 3, the narrowband light source 33 emits narrowband light NB having a wavelength limited to 400±10 nm (with its center wavelength of 405 nm). The narrowband light NB emitted from the narrowband light source 33 is introduced into a narrowband optical fiber 33a. It is to be noted that the wavelength of the narrowband light NB is not limited to 400±10 nm (with its center wavelength of 405 nm), and may be 440±10 nm (with its center wavelength of 445 nm), for example.

The coupler 36 couples the broadband optical fiber 40 and the narrowband optical fiber 33a to a light guide 43 disposed in the electronic endoscope 11. Thus, the broadband light BB and the narrowband light NB enter the light guide 43 at the same time.

The electronic endoscope 11 includes the light guide 43, a charge coupled device (CCD) 44, an analog signal processing circuit or analog front end circuit (AFE) 45, and an imaging control device 46. The light guide 43 may be a large-diameter optical fiber or a bundle fiber, which has an inlet end inserted into the coupler 36 in the light source unit 13. An outlet end of the light guide 43 faces a projection lens 48 that is mounted to the distal portion 16a. The broadband light BB and the narrowband light NB are conducted through the light guide 43, and then projected toward the body cavity through the projection lens 48 and a lightening window 49 that is mounted to an end face of the distal portion 16a. The broadband light BB and the narrowband light NB are reflected from the body cavity, and then made incident on a condenser lens 51 through a capture window 50 that is mounted to the end face of the distal portion 16a.

The CCD 44 receives the light from the condenser lens 51 on an imaging surface 44a, photoelectrically converts the received light to signal charge, and accumulates the signal charge. The accumulated signal charge is read out as an imaging signal and sent to the AFE 45. The CCD 44 is a color CCD. On the imaging surface 44a are arranged pixels of three colors, namely, B (blue) pixels, G (green) pixels, and R (red) pixels. The B pixels, G pixels, and R pixels are respectively provided with a color filter for B (blue), G (green), and R (red).

Figure 5:
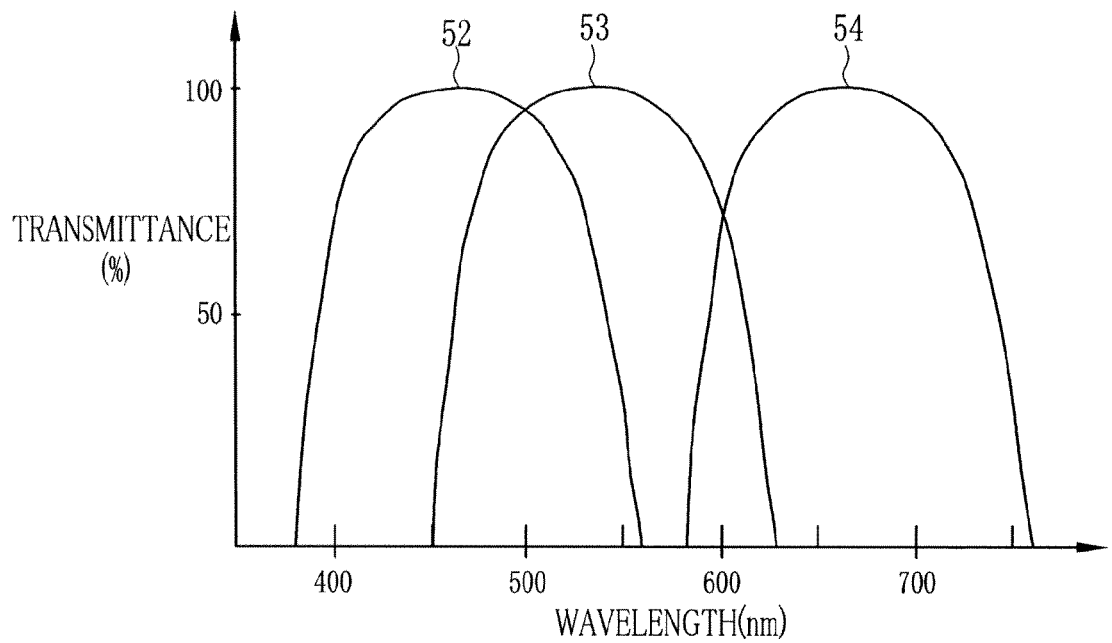
FIG. 5 is a graph showing spectral transmittances of color filters for Red (R), Green (G), and Blue (B)

The color filters for blue, green, and red have spectral transmittances 52, 53, and 54, respectively, as shown in FIG. 5. When the broadband light BB having a wavelength range of approximately 400 nm to 700 nm enters the CCD 44, the color filters for blue, green, and red transmit the broadband light BB having a wavelength corresponding to the spectral transmittances 52, 53, and 54, respectively. Here, the signal photoelectrically converted by the R pixel is referred to as red signal R, the signal photoelectrically converted by the G pixel is referred to as green signal G, and the signal photoelectrically converted by the B pixel is referred to as blue signal B.

The AFE 45 is constituted of a correlated double sampling circuit (CDS), an automatic gain control circuit (AGC), and an analog-to-digital converter (A/D), all of which are not shown in the drawings. The CDS subjects the imaging signal sent from the CCD 44 to correlated double sampling so as to eliminate noises caused by the driving of the CCD 44. The AGC amplifies the imaging signal after the noise elimination through the CDS. The A/D converts the imaging signal amplified by the AGC to a digital imaging signal having a predetermined bit number, and outputs the digital imaging signal to the processing unit 12

The imaging control device 46 is connected to the controller 59 disposed in the processing unit 12, and sends a drive signal to the CCD 44 in response to a corresponding instruction from the controller 59. Based on the drive signal from the imaging control device 46, the CCD 44 outputs the imaging signal to the AFE 45 at a designated frame rate.

As shown in FIG. 2, the processing unit 12 includes a frame memory 56, an image processing device 57, a display control circuit 58, and a receiving device 60, all of which are controlled by the controller 59. The receiving device 60 receives the blue signal B, the green signal G, and the red signal R outputted from the AFE 45 of the electric endoscope 11.

Figure 6:
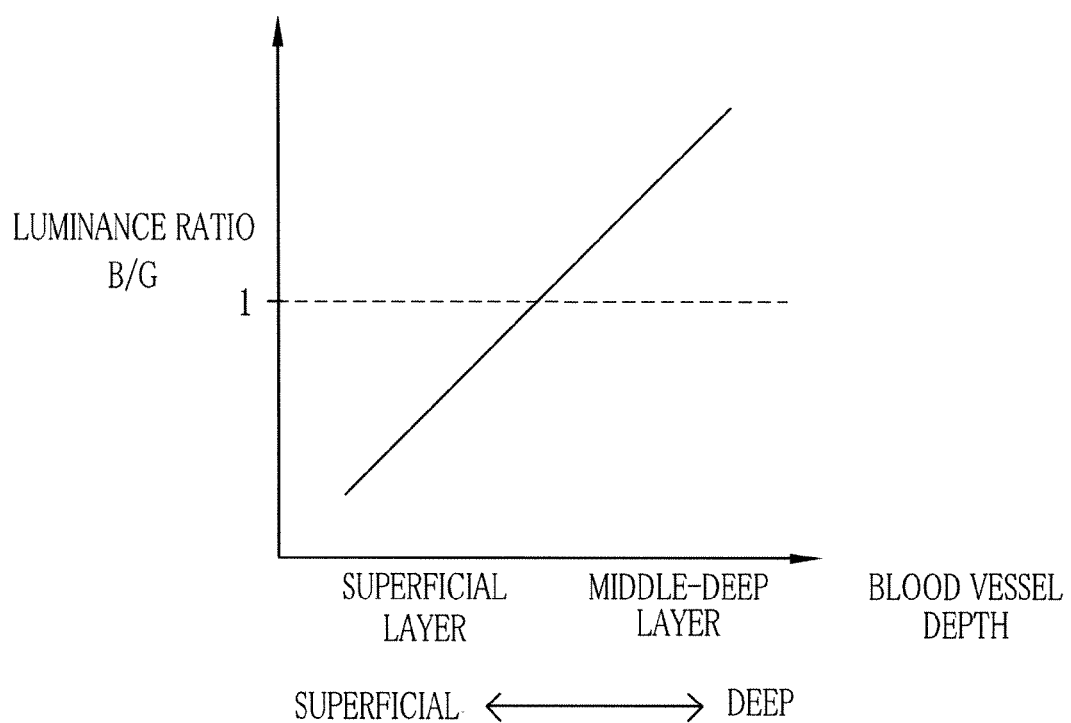
FIG. 6 is a graph showing a correlation between a luminance ratio B/G and a blood vessel depth.
Figure 7:
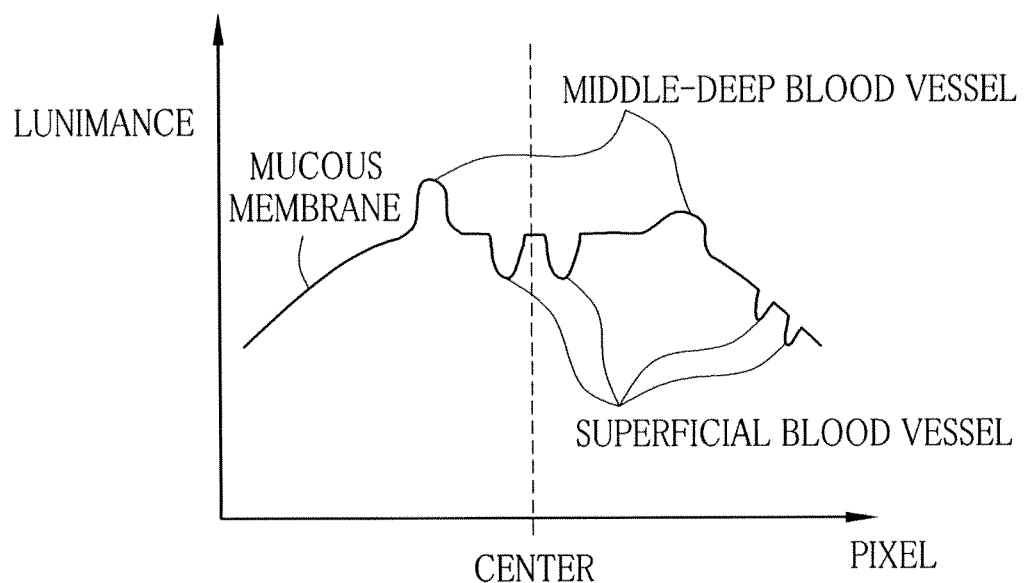
FIG. 7 is a graph showing luminance distribution at a predetermined line in a B/G image.

The image processing device 57 includes a base image generator 55, an extractor 64 having a B/G image generating section 61 and a blood vessel extracting section 63, and a blood vessel emphasized/de-emphasized image generator 65. The base image generator 55 subjects the signals outputted from the receiving device 60 to various kinds of signal processing to generate a base image. The generated base image is temporarily stored in the frame memory 56. Additionally, the blue signal B, the green signal G, and the red signal R outputted from the AFE 45 are also stored in the frame memory 56. It is to be noted that the base image may be a normal observation image which is obtained by using only the broadband light BB without using the narrowband light NB, or may be a false color image in which information on the vessel function such as oxygen saturation is subjected to false coloring. The B/G image generating section 61 generates a B/G image based on a luminance ratio B/G between pixels situated at the same position in the blue signal B and the green signal G. The luminance ratio B/G is relevant to blood depth. As shown in FIG. 6, there is a proportional relationship in which as the blood depth becomes deeper, the luminance ratio B/G becomes larger. Thus, magnitude relation expressed by "luminance of superficial blood vessel<luminance of mucous membrane<luminance of middle-deep blood vessel" is established. However, as shown in FIG. 7, the B/G image may have a luminance distribution in which the luminance becomes highest at the center, and decreases from the center toward the peripheries due to the factor such as uneven illumination, in some cases. In such a case, the magnitude relation expressed by "luminance of superficial blood vessel<luminance of mucous membrane<luminance of middle-deep blood vessel" is partially established, but may not be established totally.

Figure 8:
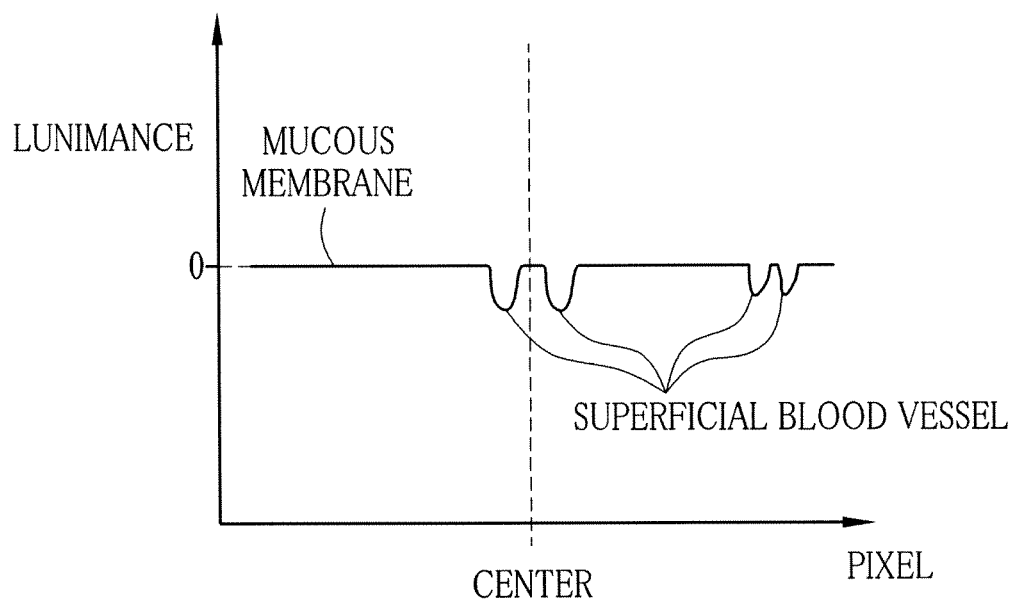
FIG. 8 is a graph showing luminance distribution at a predetermined line in a superficial-blood-vessel extracted image.

The blood vessel extracting section 63 extracts either the superficial blood vessels or the middle-deep blood vessels from the B/G image. Either the superficial blood vessels or the middle-deep blood vessels are decided to be extracted in response to the operation on an image processing button 68. The extraction of blood vessels is performed through frequency filtering. In order to extract the superficial blood vessels, a high frequency component, which is a frequency band component found predominantly in the superficial blood vessels, is extracted from the B/G image. Thereby, as shown in FIG. 8, there is obtained a superficial-blood-vessel extracted image in which the luminance of the superficial blood vessels is negative, and the luminance of the mucous membrane is approximately "zero". In the superficial-blood-vessel extracted image, only the superficial blood vessels are extracted clearly.

Figure 9:
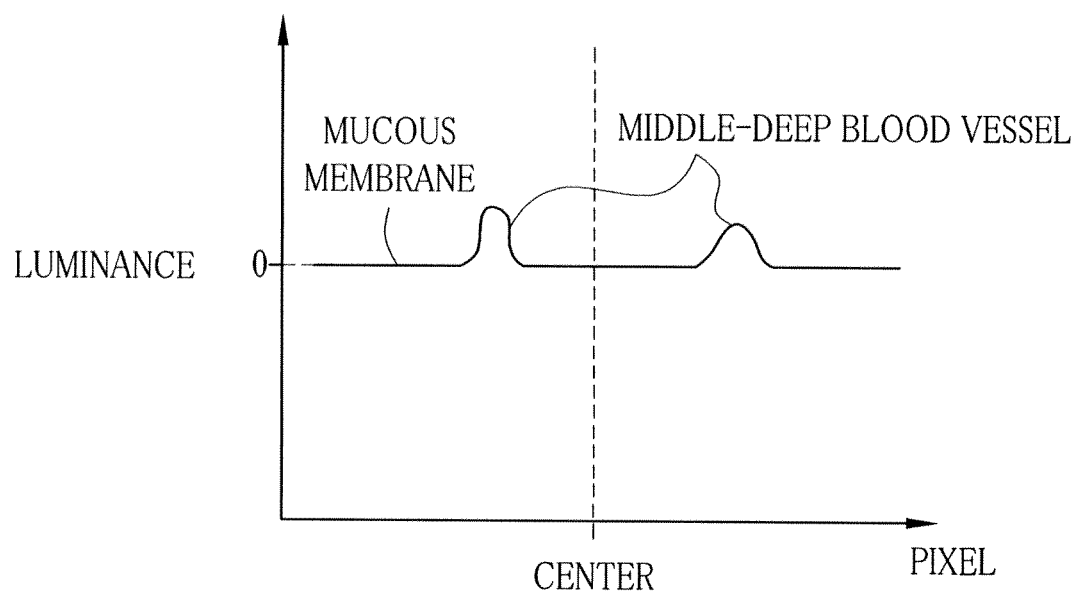
FIG. 9 is a graph showing luminance distribution at a predetermined line in a middle-deep-blood-vessel extracted image.

In contrast, in order to extract the middle-deep blood vessels, a medium frequency component, which is a frequency band component found predominantly in the middle-deep blood vessel, is extracted from the B/G image. Thereby, as shown in FIG. 9, there is obtained a middle-deep-blood-vessel extracted image in which the luminance of the middle-deep blood vessels is positive, and the luminance of the mucous membrane is approximately "zero". In the middle-deep-blood-vessel extracted image, only the middle-deep blood vessels are extracted clearly.

Since the luminance of the mucous membrane is approximately "0" after the frequency filtering as described above, only the blood vessels can be extracted. Further, the magnitude relation expressed by "luminance of superficial blood vessel<luminance of mucous membrane<luminance of middle-deep blood vessel" described above is established in a wide range.

The blood vessel emphasized/de-emphasized image generator 65 generates a blood vessel emphasized/de-emphasized image, in which the superficial blood vessels or the middle-deep blood vessels are emphasized/de-emphasized, based on the base image and the superficial-blood-vessel extracted image or the middle-deep-blood-vessel extracted image. Emphasizing or de-emphasizing is decided to be performed in response to the operation on the image processing button 68. The blood vessel emphasized/de-emphasized image is obtained by adding/subtracting the superficial-blood-vessel extracted image or the middle-deep-blood-vessel extracted image to/from the base image, while setting the portion of the mucous membrane of each of the superficial-blood-vessel extracted image and the middle-deep-blood-vessel extracted image as the threshold value.

Figure 10:
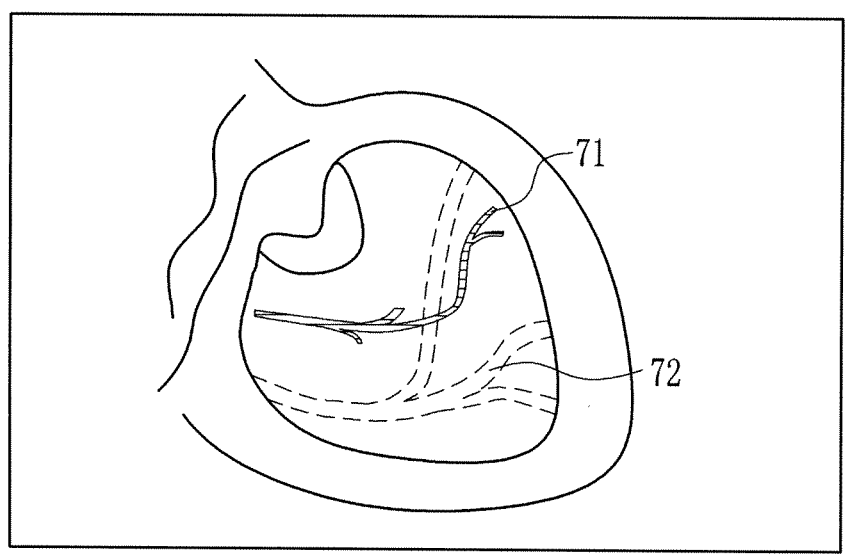
FIG. 10 is a view of an image in which superficial blood vessels are emphasized and middle-deep blood vessels are de-emphasized.
Figure 11:
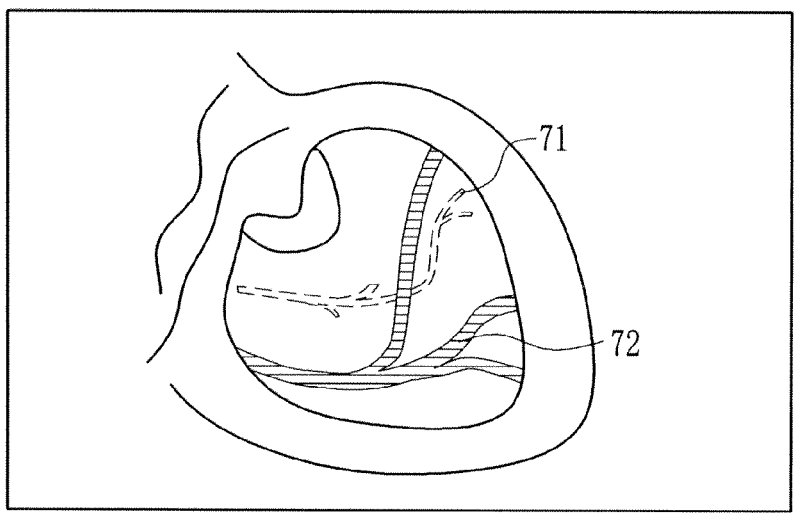
FIG. 11 is a view of an image in which the superficial blood vessels are de-emphasized and the middle-deep blood vessels are emphasized.

The display control circuit 58 displays the blood vessel emphasized/de-emphasized image on the monitor 14. For example, as shown in FIG. 10, in the case where superficial blood vessels 71 extracted from the B/G image are emphasized in the blood vessel emphasized/de-emphasized image, the superficial blood vessels 71 are more conspicuous than middle-deep blood vessels 72, and therefore diagnosis focusing on only the superficial blood vessels 71 can be conducted. In contrast, as shown in FIG. 11, in the case where the middle-deep blood vessels 72 extracted from the B/G image are emphasized in the blood vessel emphasized/de-emphasized image, the middle-deep blood vessels 72 are more conspicuous than the superficial blood vessels 71, and therefore diagnosis focusing on only the middle-deep blood vessels 72 can be conducted.

Since only the blood vessels to be focused on is extracted from the B/G image, and based on the blood-vessel extracted image, the blood vessel emphasized/de-emphasized image is generated as described above, it is possible to surely emphasize only the blood vessels to be focused on without deleting information on the portions other than the blood vessels, for example, information on protrusions and recesses in the observed portion. Accordingly, since it is possible to provide users with much information useful for diagnosis such as the information on protrusions and recesses in the observed portion in addition to the information on blood vessels, diagnostic performance can be improved. Further, since the superficial blood vessels and the middle-deep blood vessels are separately extracted emphasized/de-emphasized, the diagnosis focusing on the superficial blood vessels and the diagnosis focusing on the middle-deep blood vessels can be conducted.

Note that, when uneven illumination hardly occurs, namely when the magnitude relation expressed by "luminance of superficial blood vessel<luminance of mucous membrane<luminance of middle-deep blood vessel" described above is established in a wide range of the B/G image, it is not necessary to perform the blood vessel extraction processing through the frequency filtering, and the B/G image may be directly combined with the base image. However, if the B/G image is directly combined with the base image when the above magnitude relation is not established in a wide range, the blood vessels located at the center are thickly highlighted more than the blood vessels located at the peripheries. Therefore, it is not preferable that the blood vessel extraction processing is omitted.

Figure 12:
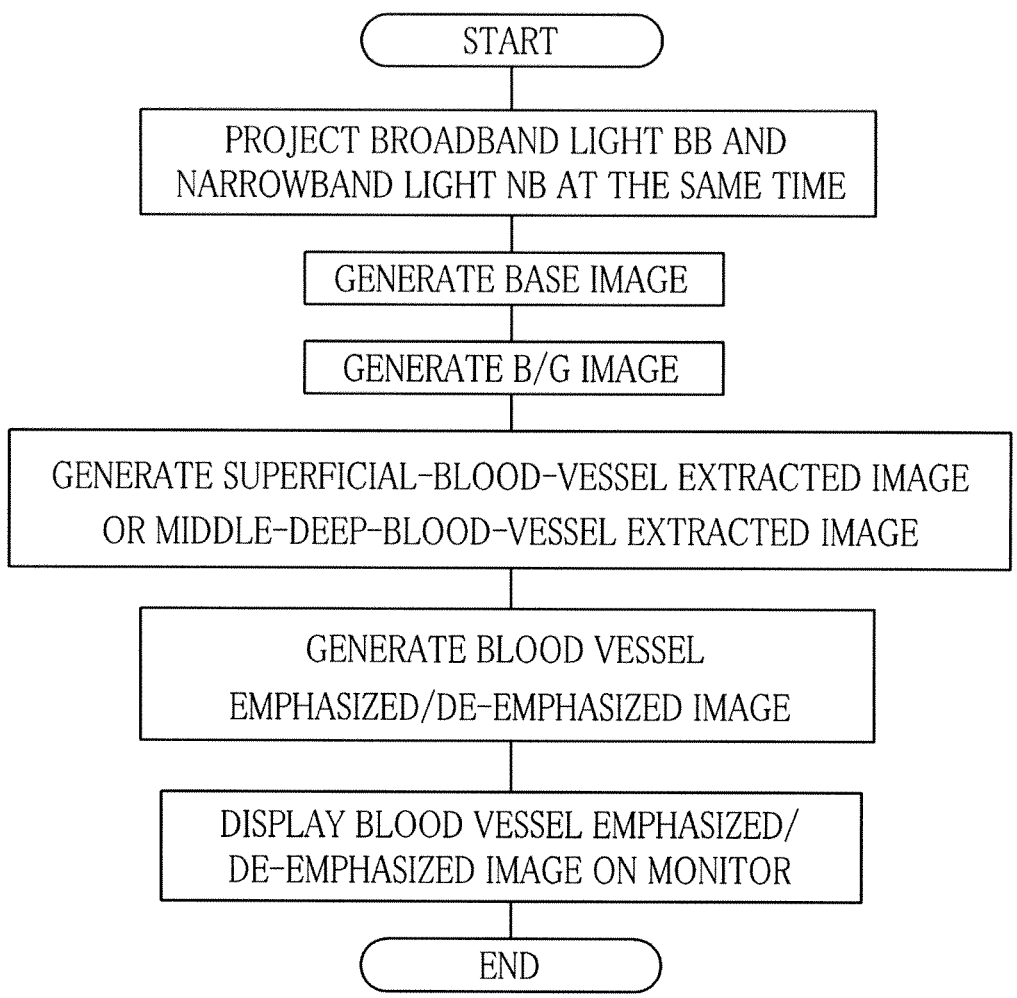
FIG. 12 is a flowchart illustrating an operation of the present invention.

Next, an operation of the above embodiment is explained by referring to the flowchart shown in FIG. 12. The broadband light BB and the narrowband light NB emitted from the light source unit 13 are simultaneously projected toward the observed portion in the body cavity through the light guide 43. The light reflected from the observed portion is imaged by the color CCD 44 so as to obtain the blue signal B, green signal G, and red signal R. Based on the blue signal B, green signal G, and red signal R thus obtained, the base image is generated. The generated base image, the blue signal B, green signal G, and red signal R are temporarily stored in the frame memory 56.

Next, the B/G image generating section 61 generates the B/G image based on the luminance ratio B/G between the blue signal B and the green signal G. After the B/G image is generated, the blood vessel extracting section 63 extracts the superficial blood vessels or the middle-deep blood vessels from the B/G image. Thereby, the superficial-blood-vessel extracted image or the middle-deep-blood-vessel extracted image is obtained. Either the superficial blood vessels or the middle-deep blood vessels are decided to be extracted in response to the operation on the image processing button 68. When either the superficial blood vessels or the middle-deep blood vessels are extracted from the B/G image, based on the base image and either the superficial-blood-vessel extracted image or the middle-deep-blood-vessel extracted image, there is generated the blood vessel emphasized/de-emphasized image in which the superficial blood vessels or the middle-deep blood vessels are emphasized/de-emphasized. The generated blood vessel emphasized/de-emphasized image is converted into a signal, which can be displayed on the monitor, by the display control circuit 58, and then displayed on the monitor 14 as shown in FIG. 10 or FIG. 11.

A second embodiment of the present invention is configured to cope with the case where the superficial blood vessels are not sufficiently resolved because of the too wide bandwidth of the narrowband light NB. According to the second embodiment, the base image is generated by a method different from that of the first embodiment. The description about the same features will be omitted. For example, for the purpose of generating the base image from the imaging signal obtained by simultaneously projecting the broadband light BB and the narrowband light NB, it is preferable that the process for eliminating the narrowband component from the base image is performed. This process is performed based on the correlation among the output values of the B pixels, G pixels, and R pixels in the color CCD 44. Further, before projection of the broadband light BB and the narrowband light NB, the narrowband light source 33 is turned off, and only the broadband light BB is projected toward the inside of the subject, such that the base image containing no narrowband component can be generated without special image processing. Furthermore, if the blue signal B is not used at the time of generating the base image, the base image containing no narrowband component also can be generated.

When the middle-deep blood vessels are emphasized/de-emphasized based on the base image containing no narrowband component, the processing of the superficial blood vessels using the high frequency component or the like is not performed unlike the first embodiment, and only the middle-deep blood vessels are extracted using the middle to low frequency component or the like, and then the extracted middle-deep blood vessels are emphasized/de-emphasized.

A third embodiment of the present invention is configured to cope with the case where there are few superficial blood vessels in the observation area and therefore the superficial blood vessels are not sufficiently resolved. According to the third embodiment, the base image is generated by a method different from that of the first embodiment. The description about the same features will be omitted. At first, the blue signal B, green signal G, and red signal R obtained by imaging the broadband light BB and the narrowband light NB simultaneously projected are subjected to frequency conversion, so as to derive a frequency component corresponding to the superficial blood vessels. At this time, if the frequency component is low, information on the narrowband light is not used to generate the base image. The method for generating the base image is described above, and therefore the description thereof will be omitted. Additionally, the emphasizing/de-emphasizing of the middle-deep blood vessels based on the base image containing no narrowband component is also describe above, and therefore the description thereof will be omitted.

According to a fourth embodiment of the present invention, resolving power of the superficial blood vessels is judged by a method different from those of the second and third embodiments, and then the base image is generated by a method different from that of the first embodiment. The description about the same features will be omitted. At first, correlation between the blue signal B and the green signal G obtained by imaging the broadband light BB and narrowband light NB simultaneously projected is derived. As a result, if similarity between the blue signal B and the green signal G is high, it is considered that the superficial blood vessels are not sufficiently resolved, and the information on the narrowband light is not used to generate the base image. The method for generating the base image and the emphasizing/de-emphasizing of the middle-deep blood vessel based on the base image containing no narrowband component are describe above, and therefore the descriptions thereof will be omitted.

Figure 13:
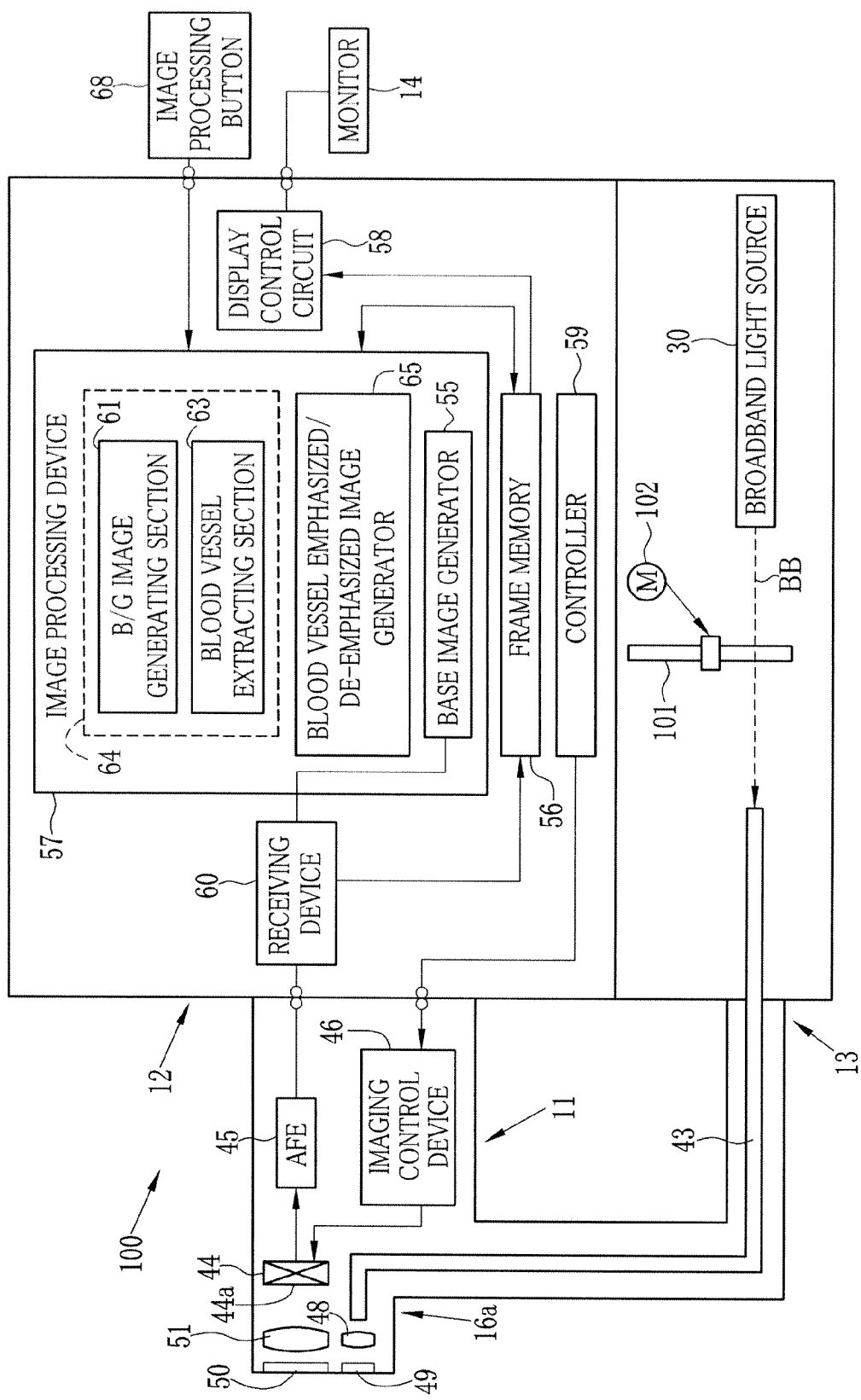
FIG. 13 is a block diagram illustrating an electrical configuration of an endoscope system according to a second embodiment of the present invention.
Figure 14:
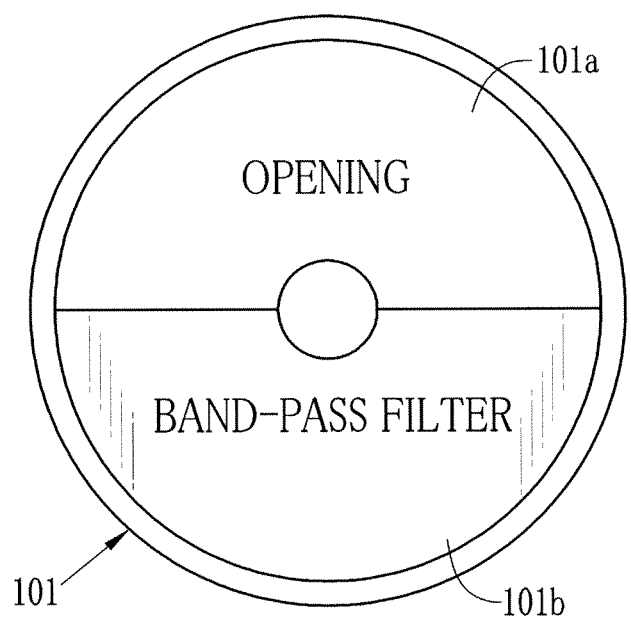
FIG. 14 is a schematic view of a rotation filter.

According to a fifth embodiment of the present invention, the broadband light BB and the narrowband light NB are projected separately from each other in a sequential manner, unlike the first to fourth embodiments in which the broadband light BB and the narrowband light NB are projected simultaneously. As shown in FIG. 13, in an electric endoscope system 100 of the fifth embodiment, in order to project the broadband light BB and the narrowband light NB separately from each other in a sequential manner, a rotation filter 101 and a motor 102 for rotating the rotation filter 101 at a predetermined speed are used. As shown in FIG. 14, the rotation filter 101 has an opening 101a and a band-pass filter 101b which are arranged along a circumferential direction. The broadband light BB emitted from the broadband light source 30 is directly transmitted through the opening 101a. The narrowband light NB having a wavelength of 400 nm to 410 nm with its center wavelength of 405 nm is transmitted through the band-pass filter 101b. In accordance with the rotation of the rotation filter 101, the broadband light BB and the narrowband light NB are projected toward the light guide 43 separately from each other in a sequential manner.

As described above, since the broadband light BB and the narrowband light NB are projected separately from each other in a sequential manner in the fifth embodiment, the method for generating the base image and the method for generating the B/G image of the fifth embodiment are different from those of the first to fourth embodiments using the simultaneous projection method. The other features of the fifth embodiment are the same as those of the first to fourth embodiments. For the purpose of generating the base image, the broadband signal obtained by projecting and imaging the broadband light BB is combined with the narrowband signal obtained by projecting and imaging the narrowband light NB. Further, for the purpose of generating the B/G image, the luminance ratio between the output value of the B pixel in the narrowband signal and the output value of the G pixel in the broadband signal is preferably used. Note that, the base image may be generated using only the broadband signal.

Although the superficial blood vessels or the middle-deep blood vessels are extracted using the frequency filtering in the above embodiments, the present invention is not limited thereto. As long as the blood vessels can be extracted, any other processing circuits may be used. Further, although either the superficial blood vessels or the middle-deep blood vessels are selectively emphasized/de-emphasized in the above embodiments, the present invention is not limited thereto. Both the superficial blood vessels and the middle-deep blood vessels may be emphasized/de-emphasized. Furthermore, in the case where there are blood vessels of three layers, namely superficial blood vessels, middle-deep blood vessels, and deep blood vessels, the blood vessels of three layers may be emphasized/de-emphasized, respectively.

Various changes and modifications are possible in the present invention and may be understood to be within the present invention.

What is claimed is:

1. An endoscope system comprising:
   an illumination device for projecting illumination light toward a subject;
   an image capturing device for capturing an image of light reflected from said subject;
   a base image generator for generating a base image based on an imaging signal obtained by the image capturing device;
   an extractor for extracting first-layer blood vessels located at a particular depth from said imaging signal so as to generate a first-layer-blood-vessel extracted image and extracting second-layer blood vessels located at a depth deeper than said first-layer blood vessels from said imaging signal so as to generate a second-layer-blood-vessel extracted image;
   a blood vessel emphasized/de-emphasized image generator for generating a blood vessel emphasized/de-emphasized image, in which said first-layer blood vessels or said second-layer blood vessels are emphasized or de-emphasized, by adding said first-layer-blood-vessel extracted image or said second-layer-blood-vessel extracted image to said base image or subtracting said first-layer-blood-vessel extracted image or said second-layer-blood-vessel extracted image from said base image; and
   a displaying device for displaying said blood vessel emphasized/de-emphasized image, wherein said image capturing device captures an image of said subject by a color imaging element,
wherein said extractor includes:
a B/G image generating section for generating a B/G image based on a luminance ratio between a blue signal outputted from a blue pixel of said imaging element and a green signal outputted from a green pixel of said imaging element,
wherein a magnitude relation of luminance of said first-layer blood vessels to luminance of mucous membrane and to luminance of middle-deep blood vessels is set such that the luminance of said first-layer blood vessels is less than the luminance of mucous membrane which is less than the luminance of middle-deep blood vessels and the magnitude relation is established in said B/G image; and
a blood vessel extracting section for extracting said first-layer blood vessels located at a particular depth from said B/G image so as to generate said first-layer-blood-vessel extracted image and extracting said second-layer blood vessels located at a depth deeper than said first-layer blood vessels from said B/G image so as to generate said second-layer-blood-vessel extracted image, and
wherein said blood vessel extracting section extracts a first frequency component containing said first-layer blood vessels from said B/G image so as to generate said first-layer-blood-vessel extracted image in which the luminance of said first-layer blood vessels is negative and the luminance of said mucous membrane is zero, or extracts a second frequency component containing said second-layer blood vessels from said B/G image so as to generate said second-layer-blood-vessel extracted image in which the luminance of said first-layer blood vessels is positive and the luminance of said mucous membrane is zero.

2. The endoscope system as defined in claim 1, wherein said illumination device projects broadband light and narrowband light toward said subject at the same time, and said base image generator generates a first base image based on said imaging signal obtained by capturing an image of said subject projected with said broadband light and said narrowband light at the same time.

3. The endoscope system as defined in claim 2, wherein said base image generator generates a second base image without using information on said narrowband light when a bandwidth of said narrowband light comprises a predetermined width, and
wherein said blood vessel emphasized/de-emphasized image generator generates a blood vessel emphasized/de-emphasized image in which only said second-layer blood vessels are emphasized or de-emphasized by adding only said second-layer-blood-vessel extracted image to said second base image or subtracting only said second-layer-blood-vessel extracted image from said second base image in a case where resolution of said first-layer blood vessels is low, and generates a blood vessel emphasized/de-emphasized image in which said first-layer blood vessels or said second-layer blood vessels are emphasized or de-emphasized by adding said first-layer-blood-vessel extracted image or said second-layer-blood-vessel extracted image to said first base image or subtracting said first-layer-blood-vessel extracted image or second-layer-blood-vessel extracted image from said first base image in a case where the resolution of the first-layer blood vessels is not low.

4. The endoscope system as defined in claim 2, wherein said base image generator derives a first frequency component corresponding to said first-layer blood vessels by subjecting said imaging signal to frequency conversion, and when said derived first frequency component is lower than a predetermined value, said base image generator determines that resolution of said first-layer blood vessels is low, and generates a second base image without using information on said narrowband light, and
wherein said blood vessel emphasized/de-emphasized image generator generates a blood vessel emphasized/de-emphasized image in which only said second-layer blood vessels are emphasized or de-emphasized by adding only said second-layer-blood-vessel extracted image to said second base image or subtracting only said second-layer-blood-vessel extracted image from said second base image in a case where the resolution of said first-layer blood vessels is low, and generates a blood vessel emphasized/de-emphasized image in which said first-layer blood vessels or said second-layer blood vessels are emphasized or de-emphasized by adding said first-layer-blood-vessel extracted image or said second-layer-blood-vessel extracted image to said first base image or subtracting said first-layer-blood-vessel extracted image or second-layer-vessel-extracted image from said first base image in a case where the resolution of said first-layer blood vessels is not low.

5. The endoscope system as defined in claim 2, wherein said image capturing device captures an image of said subject by a color imaging element,
said base image generator derives a correlation between an output value of a blue pixel of said imaging element and an output value of a green pixel of said imaging element in said imaging signal obtained by the image capturing, and generates a second base image without using information on said narrowband light in a case where resolution of said first-layer blood vessels is determined to be low based on similarity between said output value of said blue signal and said output value of said green signal, and
said blood vessel emphasized/de-emphasized image generator generates a blood vessel emphasized/de-emphasized image in which only said second-layer blood vessels are emphasized or de-emphasized by adding only said second-layer-blood-vessel extracted image to said second base image or subtracting only said second-layer-blood-vessel extracted image from said second base image in a case where the resolution of said first-layer blood vessels is low, and generates a blood vessel emphasized/de-emphasized image in which said first-layer blood vessels or said second-layer blood vessels are emphasized or de-emphasized by adding said first-layer-blood-vessel extracted image or said second-layer-blood-vessel extracted image to said first base image or subtracting said first-layer-blood-vessel extracted image or second-layer-blood-vessel extracted image from said first base image in a case where the resolution of said first-layer blood vessels is not low.

6. The endoscope system as defined in claim 5, wherein when the resolution of said first-layer blood vessels is low, said base image generator generates the second base image without using said output value of said blue pixel.

7. The endoscope system as defined in claim 1, wherein said illumination device projects broadband light toward said subject in a case where resolution of said first-layer blood vessels is low, and projects said broadband light and said narrowband light toward said subject at a same time in a case where the resolution of said first-layer blood vessels is not low, said base image generator generates a first base image based on said imaging signal obtained by capturing an image of said subject projected with said broadband light and said narrowband light at the same time in the case where the resolution of said first-layer blood vessels is not low, and generates a second based image based on said imaging signal obtained by capturing an image of said subject projected with only said broadband light in the case where the resolution of said first-layer blood vessels is low, and said blood vessel emphasized/de-emphasized image generator generates a blood vessel emphasized/de-emphasized image in which only said second-layer blood vessels are emphasized or de-emphasized by adding only said second-layer-blood-vessel extracted image to said second base image or subtracting only second-layer-blood-vessel extracted image from said second base image in the case where the resolution of said first-layer blood vessels is low, and generates a blood vessel emphasized/de-emphasized image in which said first-layer blood vessels or said second-layer blood vessels are emphasized or de-emphasized by adding said first-layer-blood-vessel extracted image or said second-layer-blood-vessel extracted image to said first base image or subtracting said first-layer-blood-vessel extracted image or second-layer-blood-vessel extracted image from said first base image in the case where the resolution of said first-layer blood vessels is not low.

8. An endoscope system as defined in claim 1, wherein
said illumination device projects broadband light and narrowband light separately toward said subject in a sequential manner, and
said base image generator generates said base image based on a broadband signal obtained by capturing an image of said subject projected with said broadband light and a narrowband signal obtained by capturing an image of said subject projected with said narrowband light.

9. The endoscope system as defined in claim 8, wherein information on a blood vessel depth of said first-layer blood vessels and information on a blood vessel depth of said second-layer blood vessels are derived from a luminance ratio between said narrowband signal and said broadband signal.

10. The endoscope system as defined in claim 1, wherein said first-layer blood vessels include superficial blood vessels, and said second-layer blood vessels include middle-deep blood vessels.

11. The endoscope system as defined in claim 1, wherein the extractor separately extracts the first-layer blood vessels and second-layer blood vessels.

12. The endoscope system as defined in claim 1, wherein the blood vessel emphasized/de-emphasized image generator sets a portion of mucous membrane of each of the first-layer-blood-vessel extracted image and the middle second-layer-blood-vessel extracted image as a threshold value.

* * * * *